(12) United States Patent
Klimant

(10) Patent No.: US 6,770,220 B1
(45) Date of Patent: Aug. 3, 2004

(54) PRODUCTION AND USE OF LUMINESCENT MICROPARTICLES AND NANOPARTICLES

(75) Inventor: Ingo Klimant, Regensburg (DE)

(73) Assignee: Presens Precision Sensing GmbH, Neuburg (DE)

( * ) Notice: Subject to any disclaimer, the term of this patent is extended or adjusted under 35 U.S.C. 154(b) by 3 days.

(21) Appl. No.: 10/031,506

(22) PCT Filed: Jul. 17, 2000

(86) PCT No.: PCT/EP00/06832

§ 371 (c)(1),
(2), (4) Date: Jan. 15, 2002

(87) PCT Pub. No.: WO01/06227

PCT Pub. Date: Jan. 25, 2001

(30) Foreign Application Priority Data

Jul. 15, 1999 (DE) ......................... 199 33 104

(51) Int. Cl.⁷ ............................................. G01N 33/58
(52) U.S. Cl. .............................. 252/301.36; 252/408.1; 435/181; 524/54.1; 530/811; 530/816; 436/172
(58) Field of Search .................. 501/32; 252/301.36, 252/301.4 R, 408.1, 301.16; 435/181; 525/511.1; 530/811, 816; 436/172

(56) References Cited

U.S. PATENT DOCUMENTS 5,573,909 A * 11/1996 Singer et al. .................. 435/6
5,786,219 A * 7/1998 Zhang et al. ................. 436/523

FOREIGN PATENT DOCUMENTS

| GB | 2 132 348 A | 4/1984 |
| GB | 2132348 | * 7/1984 |
| JP | 62 148580 A | 7/1987 |
| WO | 95 14928 A | 6/1995 |
| WO | 96 21154 A | 7/1996 |
| WO | 99 06821 A | 2/1999 |
| WO | WO 99/06821 | * 2/1999 |

OTHER PUBLICATIONS

Huber et al., "Optical Sensor for Seawater Salinity", 2000 Fresenius J. Anal. Chem., vol. 368, No. 2–3, pp. 196–202.*
Translation for WO 99/06821.*
Huber, C. et al., "Optical sensor for seawater salinity", 2000 Fresenius J. Anal. Chem., vol. 368, No. 2–3, pp. 196–202.
Liebsch, G. et al., "Luminescence lifetime temperature sensing based on sol–gels and poly (acrylonitrile)s dyed with ruthenium metal–ligand complexes", 1999 Adv. Mater., vol. 11, No. 15, pp. 1296–1299.

* cited by examiner

Primary Examiner—C. Melissa Koslow
(74) Attorney, Agent, or Firm—Sutherland Asbill & Brennan LLP

(57) ABSTRACT

Luminescent microparticles and nanoparticles are provided for use either as internal standards for referencing fluorescent signals, or as markers for detecting biomolecules. Luminescence dyes are incorporated in inert form into solid materials such that they are protected from the influence of chemical and biological compounds in aqueous sample constituents. The photophysical characteristics of the dyes (spectral characteristics, luminescence quantum efficiency, luminescence fading time and polarization) remain unaffected. The surface of the nanoparticles and microparticles can be provided with reactive surfaces in order to enable covalent coupling of biochemicals or to eliminate aggregation.

11 Claims, No Drawings

PRODUCTION AND USE OF LUMINESCENT MICROPARTICLES AND NANOPARTICLES

The invention relates to the composition, preparation and use of luminescent micro- and nanoparticles with long-lived luminescence. Said particles may be used either as internal standards for referencing fluorescence or phosphorescence signals (luminescence signals) or as markers for labeling and detecting biomolecules. Long-lived luminescent dyes are incorporated in an inert form into solid materials, i.e. shielded from the influence of chemical and biological substances in gaseous and aqueous samples. In this incorporated form, the photophysical properties of the dyes (spectral characteristics, luminescence decay time and luminescence anisotropy) remain unaffected by changing sample parameters.

The incorporating matrix selected is in particular compact inorganic materials or organic polymers which, due to their structure, exclude the uptake of biomolecules, small neutral molecules and also ionic substances. In particular, the interfering influence of molecular oxygen, an efficient fluorescence or phosphorescence quencher, on luminescence measurements is in this way eliminated or greatly reduced. The surface of said nano- and microparticles may be provided with reactive chemical groups, in order to make possible covalent coupling of biomolecules or/and luminescent indicator dyes. Furthermore, the surface may be provided with chemical groups in order to prevent the particles from aggregating.

Luminescence measurement is a very common method in biological and chemical analysis. Its attractiveness is due to its high sensitivity, versatility and also the elimination of radiation exposure by radioactive labeling reagents. In practice, luminescent markers distinguished by a high quantam yield are normally used. In most cases, the luminescence intensity of the luminescent marker is correlated with the sample parameter to be determined. Those determination methods are adversely affected by the fact that a multiplicity of factors interferes with the quantitative evaluation of luminescence intensity. Said factors may include firstly variations in the optical system (radiation intensity of the light source, detector sensitivity and transmission of the optical path), but also intrinsic optical properties of the sample (coloration or turbidity).

In order to eliminate or reduce said interfering influences, suitable methods for referencing the luminescence signals are required. WO 99/06821 (Klimant) describes a method for referencing luminescence signals, which is based on adding to the sample a luminescent reference dye which has similar (at best identical) spectral properties to the actual luminescent marker. In this way and in combination with frequence-modulated or time-resolved luminescence measurement, the intensity information is converted into a phase signal or a time-dependent parameter. In order to carry out correct referencing of the measurement signal in this way, inert luminescent reference standards are required, whose luminescence properties are not adversely affected by the sample parameters. Suitable for this purpose are, for example, phosphorescent inorganic solids such as, for example, Cr(III)-doped mixed oxides which can be admixed to the sample in powder form. On the other hand, it is also possible for this purpose to incorporate long-lived luminescent dyes into carriers made of organic or inorganic materials and admix the sample therewith.

Another type of interference of the quantitative evaluation of fluorescence intensity signals is the occurrence of intrinsic fluorescence in the sample. Natural samples such as blood or serum, in particular, can have a multiplicity of fluorescent substances. If the signal intensity of the fluorimetric assay is very low, intrinsic fluorescence may even render the measurement impossible. A widespread method for removing the actual luminescence signal from the unspecific background signal is to use luminescent dyes with long-lived emission as markers. It is possible, with the aid of time-resolved luminescence techniques, to separate by time the delayed measurement signal from the short-lived background fluorescence. This method uses mainly phosphorescent chelates of the rare earth metals (in particular those of europium or terbium). However, said dyes have the disadvantage that they can only be excited by UV light sources. Moreover, the chelates are often unstable when used in soluble form in aqueous systems, i.e. the ligands are lost. However, suitable long-lived markers are potentially also luminescent metal/ligand complexes, in particular those with ruthenium(II) as central atom. If these dyes are added in soluble form to aqueous systems, their luminescence is normally quenched by molecular oxygen, strong oxidants or reducers.

Furthermore, it is also possible, for example for determining the pH, the concentration or activity of ions or small molecules, to use luminescent indicators whose luminescence intensity depends on the concentration or activity of the parameter to be determined, for example an analyte or the pH, due to direct or indirect interaction with the parameter to be determined, for example due to reaction with an analyte or as transducer.

All methods mentioned absolutely require the photophysical properties of the luminescent dye to be unaffected by the sample parameters. These preconditions are not met if such dyes are added in dissolved form to the sample or contacted at least indirectly with the sample. Fluoresence or phosphoresence quenching by molecular oxygen and also oxidizing and reducing quenchers cause misinterpretations of the measurement signal.

In order to have available inert long-lived luminescent markers and luminescent dyes for referencing the luminescence intensity of luminescent indicators, the luminescent dyes have to be incorporated into solid materials so that they are incapable of interacting with the sample.

The present application describes both novel luminescent micro- and nanoparticles whose luminescence properties depend negligibly, if at all, on the sample composition, and methods for the preparation thereof. In addition, possible applications of the luminescent markers or luminescent dyes, present in the form of nano- and microparticles, for referencing the luminescence intensity of luminescent indicators are described.

The application therefore relates to luminescent, in particular phosphorescent, micro- and nanoparticles containing luminescent substances, for example metal/ligand complexes with long luminescence cay times, in a solid matrix so that they are shielded from ambient chemical parameters, for example a sample, and the luminescence properties of which, such as quantam yield, spectral characteristics, luminescence cay time or/and anisotropy, are essentially independent of the particular environment, for example the particular sample composition.

"Independents" in accordance with the subject application means that the dependence of the luminescence decay time and, where appropriate, further luminescence properties on the $PO_2$ and, where appropriate, other interfering substances in the environment of the luminescent dyes which are present in the particles of the invention and are at least in indirect contact with the sample is lower then the dependence of the luminescence decay time and, where appropriate, further luminescence properties of the corresponding dyes which are at least in indirect contact with the sample, without the inventive shielding.

Preferably, the luminescence lifetime of the luminescent dyes present in the particles of the invention is in an air-saturated environment at most 20%, particularly preferably at most 15% and most preferably at most 10% shorter than in an $O_2$-free environment, in each case at room temperature. Without shielding, however, a reduction in the luminescence decay time by distinctly more than 80% is found in an air-saturated environment compared with an $O_2$-free environment.

The luminescent metal/ligand complexes are preferably compounds of transition metals such as ruthenium(II), osmium(II), rhenium(I), iridium(III), platinum(II) and palladium(II) as central atoms. The complex ligands are preferably selected from two- or/and three-dentate ligands with N-heterocycles, for example polypyridyl ligands such as 2,2'-bipyridine, bipyrazine, phenanthroline, terpyridil or derivatives thereof. Particularly preferred examples of metal/ligand complexes are the tris complexes of ruthenium (II) with 2,2'-bipyridyl, 1,10-phenanthroline, 4,4-diphenyl-2,2'-bipyridyl and 4,7-diphenyl-1,10-phenanthroline as ligands. Particular preference is furthermore given to carbonyl complexes of Re(I) with additional poly-N-heterocyclic ligands such as, for example, 2,2'-bipyridyl and 1,10-phenanthroline. Likewise, preferred metal/ligand complexes are the porphyrin complexes of Pt(II) or Pd(II) as central atom, which are distinguished by intense phosphorescence at room temperature. The luminescence decay times of said compounds are preferably $\geq 100$ nanoseconds, particularly preferably $\geq 400$ nanoseconds. According to the invention, it is also possible to use rare earth metals such as, for example, the lanthanides Tb(III) and Eu(III) or other substances as long-lived luminescent dyes.

The average size of the luminescent micro- and nanoparticles is preferably in the range from 20 $\mu$m to 10 $\mu$m, particularly preferably from 50 nm to 1 $\mu$m. The luminescent compounds are incorporated into materials which are distinguished by low permeability (i.e. low diffusion constants and low solubility) for water, quenching gaseous substances (e.g. $O_2$) and interfering substances. Examples of suitable materials are nonporous glasses, in particular glasses which have been produced, for example, from silicon-, titanium-, zirconium- or tin-containing compounds, for example alcoholates such as tin tetraalcoholates, according to a sol/gel method.

Preparation of such glasses according to standard methods leads to materials which are characterized by a microporous structure. Incorporated luminescent dyes are thus accessible for dissolved sample components and in particular oxygen and can thus be quenched. For this reason, the sol glasses described in the present invention are, in a particular preparation step, compressed by heating to an elevated temperature of, for example, 200° C. After hydrolyzing the sol/gel precursor, for example tetramethoxysilane, the solvent is stripped off under reduced pressure and the sol/gel is dried prior to the final crosslinking. In this way, a dense nonporous glass matrix is formed. Biomolecules and also chemical compounds cannot penetrate said dense matrix and therefore do not influence the luminescence properties of the incorporated dyes. Inert phosphorescent sol/gel glasses having the dyes ruthenium(II)-tris-1,10-phenanthroline and ruthenium(II)-tris-4,7-diphenyl-1,10-phenanthroline and a dye content of up to 40 mM (based on kg $SiO_2$) were produced according to said method. These materials are distinguished by intense luminescence at room temperature, which is not quenched by oxygen. Since the sol/gel phosphors are formed in the preparation process either in monolithic form or as thin films, microparticles have to be produced by powdering. Subsequent silanization of the particles leads to reactive surfaces which can be utilized for covalent coupling of luminescent indicators or biomolecules. For this, the particle surface may be provided with, for example, amino, epoxy, hydroxyl, thiol or/and carboxyl groups.

An alternative method of preparing inert luminescent particles is the use of organic polymers as embedding matrix, which are distinguished firstly by a very low gas permeability (in order to exclude oxygen) and secondly by minimum absorption of water (in order to prevent penetration of ionic compounds). Suitable polymers are polyvinyl chloride, polyvinylidene chloride, poly(meth)acrylic polymers and in particular polyacrylonitrile and also copolymers thereof.

Polyacrylonitrile (PAN) has an extremely low gas permeability, partly hydrophilic properties and a very low absorption capacity for water (approx. 2%). Moreover, the nitrile groups on the surface of the polymer particles, for example, can be saponified to give carboxyl groups or/and amide groups or converted to give amine groups, which are then available for covalent binding of various biomolecules. For this reason, polyacrylonitrile is the optimum embedding matrix for luminescent dyes as base for inert nano- and microparticles.

Furthermore, it is also possible to use polyacrylonitrile copolymers or mixed polymers with polyacrylonitrile, i.e. polymers containing acrylonitrile and additionally one or more monomers, in particular polyacrylonitrile copolymers or mixed polymers with at least 50%, preferably at least 70%, and particularly preferred at least 90%, by weight of PAN. A copolymer contains PAN and a comonomer in a polymer chain. A mixed polymer contains a PAN or PAN copolymer component in a polymer chain and at least one non-PAN component in another polymer chain. Suitable additional monomers for copolymers and mixed polymers are monomers with hydrophilic or/and reactive groups, for example acrylic acid, acrylic amines and acrylic esters, for example polyethylene glycol acrylic esters, or mixtures thereof. In this context, the hydrophilic groups are preferably concentrated on the particle surface. The hydrophilic or/and reactive groups on the surface can then be used for coupling binding partners such as biomolecules or luminescent indicator molecules. Furthermore, these groups can also contribute to preventing particle aggregation.

Luminescent micro- and nanoparticles based on polyacrylonitrile (PAN) can be prepared in various ways.

A. Precipitation of the particles from a solution of PAN or a PAN copolymer or mixed polymer in an organic solvent (mixture), for example dimethylformamide, by adding, dropwise in a controlled fashion, water, aqueous solutions, for example an NaCl solution, or other liquids which are miscible with the polymer solvent but cause a reduction in solubility and thus precipitation of the polymer with the luminescent dye. The polymer solution contains at the same time the dissolved luminescent dye. This method variant is particularly simple and therefore preferred.

B: Precipitation of the particles from a solution of PAN or a PAN copolymer or mixed polymer in an organic solvent (mixture), for example dimethylformamide, by adding, dropwise in a controlled fashion, water, aqueous solutions, for example an NaCl solution, or other liquids which are miscible with the polymer solvent, but cause precipitation of the polymer. The polymer solution contains no dissolved luminescent dye. The luminescent dye is introduced into the particles subsequently by diffusion.

C. Preparation of the particles by spraying a solution of PAN or a PAN copolymer or mixed polymer in an organic solvent (mixture), for example dimethylformamide, which contains the luminescent dye, for example, in water or ethanol, and evaporation of the solvent.

In all protocols it is possible to adjust the particle diameter specifically by altering the polymer proportion in the solution. With a decreasing proportion of polymer, the particle diameter is also reduced.

After preparing and isolating the luminescent micro- and nanoparticles, the surface can be activated by reactive carboxyl groups, for example by saponification of the surface-bound nitrile groups in base, for example concentrated sodium hydroxide solution. The carboxyl groups are required for two reasons. Firstly, it is possible to,prepare in this way stable dispersions in (pH-)buffered systems and, secondly, biomolecules and luminescent indicators can be bound covalently to the surface.

Particles of the invention, whose surface has been modified by reactive groups, may be used for covalently coupling luminescent indicators or/and biomolecules. The luminescent indicators may be compounds similar to those included in the particle matrix. In contrast to the included luminescent compounds, the luminescent indicators coupled to the surface are in contact with the environment, so that they can react to ambient chemical parameters. Particles modified in this way may be used as indicators with internal referencing.

Alternatively, or additionally, it is also possible to couple biomolecules such as toxins, hormones, hormone receptors, peptides, proteins, lectins, oligonu-cleotides, nucleic acids, antibodies, antigens, viruses and bacteria to the particle surfaces. Coupling is carried out via known methods, for example by using bifunctional linker molecules.

In addition, it is possible to use the particles as standards for referencing luminescence intensity signals in fluorimetric assays, for example for diagnostic determination of analytes.

The micro- and nanoparticles may be used on the one hand as luminescent standards for converting the luminescence intensity of luminescent indicators bound to the surface or present in the environment into phase signals or time-dependent parameters (for example for referencing the luminescence intensity signal of optical luminescence sensors, with the particles being immobilized together with a luminescent indicator in a solid phase, as described in WO99/06821 (Klimant)),and on the other hand as luminescent markers for highly sensitive detection or determination of biomolecules.

The invention therefore also relates to a method for luminometric determination of a biochemical or chemical parameter using two different luminescent dyes which have different decay times and the time or phase characteristics of the resulting luminescent response are used for generating a reference parameter for determination of said parameter, with the first luminescent dye corresponding to said parameter at least with respect to luminescence intensity and the second one essentially not corresponding to said parameter at least with respect to luminescence intensity and luminescence decay time and the method is characterized in that the second luminescent dye is used in the form of particles of the invention. The reference parameter used is preferably a ratio of the two luminescence intensity proportions, which is independent of the total intensity of the luminescence signal.

A reference parameter which may be used as an alternative is the phase shift of the luminescence response of the first luminescent dye compared to that of the second luminescent dye. In addition, the reference parameter may also be the measured phase shift of the combined signal of the signal of the first luminescent dye and the delayed reference signal of the second luminescent dye. For further details of the method and a device for carrying out the method, WO99/06821 is referred to.

Furthermore, the following examples are intended to illustrate the invention.

EXAMPLES

Example 1

Preparation of Luminescent Nanoparticles from Polyacrylonitrile and [ruthenium(II)-tris-4,7-diphenyl-1,10 phenanthroline ]$^{2+}$ 1 g of n-polyacrylonitrile (Polysciences Inc., MW 150000) is dissolved together with 10 mg of ruthenium(II)-tris-4,7-diphenyl-1,10-phenanthroline per-chlorate in 100 ml of dimethylformamide (DMF) and introduced into a 1 l glass beaker. 400 ml of $H_2O$ are slowly added dropwise to this solution with constant stirring, leading to a slight turbidity in the solution. This is followed by adding, likewise with constant stirring, 10 ml of a 5% strength sodium chloride solution, resulting in a flocculent precipitate which settles at the bottom of the beaker overnight. This precipitate contains the entire dye and is separated by centrifugation and subsequently washed three times with 250 ml of a 0.5% strength NaCl solution. In the next step, the precipitate is washed with 200 ml of ethanol in order to wash out completely the luminescent dye adsorbed on the surface. The ethanol is removed from the precipitate by centrifugation. This is followed by a last washing step in a 0.05% strength NaCl solution. The precipitate which consists of the nanoparticles is removed and taken up in 50 ml of $H_2O$.

Example 2

Preparation of Phosphorescent Nanoparticles from Polyacrylonitrile and [ruthenium(II)-tris-1,10 phenanthroline]$^{2+}$ 1 g of n-polyacrylonitrile is dissolved together with 10 mg of ruthenium(II)-tris-1,10-phenanthroline hexafluorophosphate in 100 ml of dimethylformamide and introduced into a 1 l glass beaker. 400 ml of $H_2O$ are slowly added dropwise to this solution with constant stirring, leading to a slight turbidity in the solution. This is followed by adding, likewise with constant stirring, 10 ml of a 5% strength sodium chloride solution, resulting in a precipitate which settles at the bottom of the beaker overnight. This precipitate contains approx. 90% of the dye used and is separated by centrifugation and subsequently washed three times with 250 ml of a 0.5% strength NaCl solution. In the next step, the precipitate is washed with 200 ml of ethanol in order to wash out completely the luminescent dye adsorbed on the surface. The ethanol is removed from the precipitate by centrifugation. This is followed by a last washing step in a 0.05% strength NaCl solution. The precipitate (nanoparticles) is removed and taken up in 50 ml of $H_2O$.

Example 3

Carboxylation of the Surface of the Luminescent Nanoparticles 10 ml of the particle suspension from Examples 1 or 2, having a solids content of 200 mg of polyacrylonitrile, 10 are taken up in 50 ml of a 5% strength NaOH solution The particles precipitate and the suspension is heated to 75° C. with intense stirring for 45 minutes. An intense smell of ammonia indicates hydrolysis of the nitrile groups located on the surfaces. After clearing of the turbid solution, the sodium hydroxide solution is neutralized by adding HCl and adjusted to pH 3. This results again in precipitation of the particles carboxylated on the surface, which can then be removed by centrifugation. They are finally washed in 50 ml of buffer, pH 3, removed by centrifugation and taken up in 10 ml of distilled water.

The saponification may be carried out analogously also in 8% NaOH at 25° C. for 24 h.

Example 4

Nanoparticles Consisting of a Copolymer of 90% Polyacrylonitrile and 10% Polyacrylic Acid and [ruthenium(II)-tris-4,7-diphenyl-1,10-phenanthroline]$^{2+}$ 2 g of a self-synthesized acrylonitrile/lacrylic acid 10:1 copolymer and 40 mg of [ruthenium(II)-tris-4,7-diphenyl-1,10-phenanthroline]$^{2+}$ as trimethylsilylpropanesulophonate (Ru(dphphen)$_3$TMS$_2$) are dissolved in 400 g of DMF. 1 l of $10^{-3}$ N NaOH is added dropwise with stirring and water is added to 2 l. The clear suspension is adjusted to pH 3 with 0.1 N HCl and the precipitate is removed by centrifugation. The centrifugate is washed 3 times with in each case 1.8 l of water and resuspended in 200 ml of 50 mM Na$_2$HPO$_4$ by means of ultrasound. The clear suspension is heated to approx. 80° C. for 20 min and, after cooling, again adjusted to pH 3 by adding HCl, removed by centrifugation and resuspended in 200 ml of 50 mM Na$_2$HPO$_4$ by means of ultrasound.

Example 5

Nanoparticles Comprising a Copolymer of 95% Polyacrylonitrile and 5% Polyacrylic Acid and [Ru(dphphen)$_3$]$^{2+}$ 2 g of acrylonitrile/acrylic acid 20:1 copolymer and 40 mg of Ru(dphphen)$_3$TMS$_2$ are dissolved in 400 g of DMF. 1 l of $10_{-3}$ N NaOH is added dropwise with stirring and water is added to 2 l. The clear suspension is adjusted to pH 3 with 0.1 N HCl and the, precipitate is removed by centrifugation. The centrifugate is washed 3 times with in each case 1.8 l of water and resuspended in 200 ml of 50 mM Na$_2$HPO$_4$ by means of ultrasound. The clear suspension is heated to approx. 80° C. for 20 min and, after cooling, again adjusted to pH 3 by adding HCl, removed by centrifugation and resuspended in 200 ml of 50 mM Na$_2$HPO$_4$ by means of ultrasound.

Example 6

Nanoparticles Consisting of a Copolymer of 99.5% Polyacrylonitrile and 0.5% Polyacrylic Amine and [Ru(dphphen)$_3$]$^{2+}$ 0.5 g of acrylonitrile/3-aminopropylacrylamide—200:1 copolymer and 10 mg of Ru(dphphen)3TMS$_2$ are dissolved in 100 g of DMF. 0.5 l of $10^{-3}$ N HCl is added dropwise with stirring and water is added to 1 l. The clear suspension is adjusted to pH 9 with 0.1 N NaOH and the precipitate is removed by centrifugation. The centrifugate is washed 3 times with in each case 1 l of water and resuspended in 50 ml of water by means of ultrasound. The suspension is heated to approx. 80° C. for 20 min and, after cooling, washed 2 times with water and resuspended.

Example 7

Nanoparticles Consisting of a Copolymer of 90% Polyacrylonitrile and 5% Polyacrylic Acid and 5% Polyethylene Glycol Monoethyl Ether Acrylate and [Ru(dphphen)$_3$]$^{2+}$ 0.5 g of acrylonitrile/acrylic acid/polyethylene glycol monomethyl ether acrylate 20:1:1 copolymer and 5 mg of Ru(dphphen)$_3$TMS$_2$ are dissolved in 200 g of DMF. 1 l of $10^{-3}$ N NaOH is added dropwise with stirring. The clear suspension is adjusted to pH 3 with 0.1 N HCl and the precipitate is removed by centrifugation. The centrifugate is washed 3 times with in each case 1 l of water and resuspended in 1 l of 100 mM Na$_2$HPO$_4$ by means of ultrasound. The clear suspension is adjusted to pH 3 by adding HCl, removed by centrifugation and resuspended in 200 ml of 100 mM Na$_2$HPO$_4$ by means of ultrasound. The clear suspension is heated to approx. 80° C. for 20 min and, after cooling, again adjusted to pH 3 by adding HCl, removed by centrifugation and resuspended in 200 ml of 50 mM Na$_2$HPO$_4$ by means of ultrasound.

Example 8

Nanoparticles Consisting of a Copolymer of 85% Polyacrylonitrile, 5% Polyacrylic Acid and 10% Polysulfoacrylate and [Ru(dphphen)$_3$]$^{2+}$ 0.5 g of acrylonitrile/acrylic acid/sulfopropylacrylate 20:1:2 copolymer and 50 mg of Ru(dphphen)$_3$Cl$_2$ are dissolved in 100 g of DMF. 0.5 l of $10^{-3}$ N NaOH is added dropwise with stirring. The clear suspension is adjusted to pH 3 with 0.1 N HCl and the precipitate is removed by centrifugation. The centrifugate is washed 3 times with in each case 1 l of water and resuspended in 100 ml of 50 mM Na2HPO$_4$ by means of ultrasound. The clear suspension is heated to approx. 80° C. for 20 min and, after cooling, again adjusted to pH 3 by adding HCl, removed by centrifugation and resuspended in 100 ml of 50 mM Na$_2$HPO$_4$ by means of ultrasound.

Example 9

Characterization of Luminescent Particles Based on Polyacrylonitrile or Polyacrylonitrile Copolymers The particles listed, having an average diameter of from 20 to 100 nm and containing the luminescent dye ruthenium (II)-tris-4,7-diphenyl-1,10-phenanthroline were measured in a 20 mM phosphate buffer (pH 7) at 20° C. The nanoparticles were dispersed in a sample. The results are shown in Table I below.

TABLE 1

Characterization of various phosphorescent nanoparticles based on polyacrylonitrile particles
(Diameter of the particles listed (20–100 nm), dye in all cases: the ruthenium(II)-tris-4,7-diphenyl-1,10-phenanthroline complex. All measurements were carried out in a 20 mM phosphate buffer (pH 7) at 20° C. The nanoparticles were dispersed in the sample.

| Sensor | Base monomer (= acrylonitrile) [% (w/w)] | Comonomer(s) | Comonomer(s) [% (w/w)] | Air-saturated relative phosphorescence intensity I | decay time [$\mu s$] | $N_2$-saturated decay time [$\mu s$] | oxygen quenching (decrease in decay time between 0 and 200 hPa $pO_2$) in % |
|---|---|---|---|---|---|---|---|
| Dye dissolved in water | — | — | — | 12 | 0.90 | 4.40 | 85 |
| 1 (Ex. 1) | 100.0 | — | 0.0 | 23.81 | 5.69 | 6.20 | 8.2 |
| 2 | 90.0 | acrylic acid | 10.0 | 26.00 | 6.10 | 6.36 | 4.1 |
| 3 | 87.0 | acrylic acid | 13.0 | 19.81 | 5.55 | 6.17 | 10.0 |
| 4 | 76.9 | acrylic acid | 23.1 | 18.07 | 5.89 | 5.91 | 0.3 |
| 5 (Ex. 5) | 95.0 | acrylic acid | 5.0 | 15.24 | 5.78 | 6.11 | 5.4 |
| 6 | 95.0 | ethylene glycol monoethyl ether acrylate | 5.0 | 19.36 | 6.01 | 6.24 | 3.7 |
| 7 (Ex. 7) | 90.0 | acrylic acid ethylene glycol monoethyl ether acrylate | 5.0, 5.0 | 17.23 | 5.38 | 5.94 | 9.4 |
| 8 | 63.4 | acrylic acid, ethylene glycol monoethyl ether acrylate | 8.3, 8.3 | 19.46 | 6.00 | 6.16 | 2.6 |
| 9 (Ex. 8) | 87.0 | acrylic acid, acrylosulfonic acid | 4.3, 8.7 | 16.05 | 5.36 | 5.98 | 10.4 |
| 10 | 95.0 | primary acrylic amine (ester, —CO(CH$_2$)$_2$NH$_2$) | 5.0 | 25.11 | 5.59 | 5.96 | 6.2 |
| 11 | 90.0 | primary acrylic amine (ester, —CO(CH$_2$)$_2$NH$_2$) | 10.0 | 18.64 | 5.75 | 5.82 | 1.2 |
| 12 (Ex. 6) | 99.5 | primary acrylic amine (amine, —NH(CH$_2$)$_2$NH$_2$) | 0.5 | 16.52 | 5.27 | 5.90 | 10.7 |

What is claimed is:

1. A luminescent micro- or nanoparticle, wherein said micro- or nanoparticle comprises polyacrylonitrile or polyacrylonitrile copolymers and luminescent substances having long luminescence decay times wherein said luminescent substances are essentially shielded from ambient chemical, biochemical and gaseous parameters, wherein said luminescent substances are metal/ligand complexes of ruthenium (II), osmium(II), rhenium(I), iridium(III), platinum(II) and palladium(II) as central atom and wherein the luminescent substances are complexes with 2- or 3-dentate polypyridyl ligands.

2. The luminescent micro- or nanoparticle as claimed in claim 1, wherein said 2- or 3-dentate polypyridyl ligands are selected from the group consisting of 2,2'-bipyridine, bipyrazine, phenanthroline, terpyridyl and derivatives thereof.

3. The luminescent micro- or nanoparticle as claimed in claim 1, wherein the luminescent compounds are the tris complexes of ruthenium(II) with 2,2'-bipyridyl, 1,10-phenanthroline, 4,4-diphenyl-2,2'-bipyridyl and 4,7-diphenyl-1,10-phenanthroline as ligands.

4. A luminescent micro- or nanoparticle, wherein said micro- or nanoparticle comprises polyacrylonitrile or polyacrylonitrile copolymers and luminescent substances having long luminescence decay times wherein said luminescent substances are essentially shielded from ambient chemical, biochemical and gaseous parameters, wherein the luminescent substances are carbonyl complexes of Re(I) with additional diimine ligands.

5. The luminescent micro- or nanoparticle as claimed in claim 4, wherein said diimine ligands are selected from the group consisting of derivatives of 2,2'-bipyridyl and 1,10-phenanthroline.

6. A method for preparing luminescent micro- and nanoparticles, wherein said micro- or nanoparticles comprise an organic polymer which distinguishes itself by low absorption of water and/or minimum gas permeability, comprising, precipitating luminescent micro- and nanoparticles from a polymer solution in which the luminescent compound is present in soluble form by adding a liquid dropwise, with the liquid being miscible with the polymer solvent but causing a reduction in the solubility of the polymer.

7. The method as claimed in claim 6, wherein said micro- or nanoparticles are precipitated from a solution comprising dimethylformamide and polyacrylonitrile or polyacrylonitrile copolymer, in which the luminescent compound is present in soluble form, by adding water or an aqueous solution dropwise.

8. The method as claimed in claim 6, wherein the micro- or nanoparticle diameter is adjusted by varying the polymer content of the solution.

9. A method for preparing luminescent micro- and nanoparticles, wherein said micro- or nanoparticles comprise an organic polymer which distinguishes itself by low absorption of water and/or minimum gas permeability, comprising, forming the micro- or nanoparticles by spraying a polymer solution in which the luminescent compound is present in soluble form and evaporating the solvent.

10. The method as claimed in claim 9, wherein the particle diameter is adjusted by varying the polymer content of the spray solution.

11. A method for luminometric determination of a biochemical or chemical parameter comprising using two different luminescent dyes which have different decay times and wherein the time or phase characteristics of the resulting luminescent response are used for generating a reference parameter for determination of said parameter, with the first luminescent dye corresponding to said parameter at least with respect to luminescence intensity and the second one not corresponding to said parameter at least with respect to luminescence intensity and luminescence decay time, wherein second luminescent dye is in the form of a luminescent micro- or nanoparticle, wherein said micro- or nanoparticle comprises polyacrylonitrile or polyacrylonitrile copolymers and luminescent substances having long luminescence decay times wherein said luminescent substances are essentially shielded from ambient chemical, biochemical and gaseous parameters.

\* \* \* \* \*